United States Patent
O'Rear

(10) Patent No.: US 8,076,122 B2
(45) Date of Patent: *Dec. 13, 2011

(54) PROCESS FOR INTEGRATING CONVERSION OF HYDROCARBONACEOUS ASSETS AND PHOTOBIOFUELS PRODUCTION USING AN ABSORPTION TOWER

(75) Inventor: Dennis J. O'Rear, Petaluma, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 1144 days.

This patent is subject to a terminal disclaimer.

(21) Appl. No.: 11/828,071

(22) Filed: Jul. 25, 2007

(65) Prior Publication Data

US 2009/0028775 A1 Jan. 29, 2009

(51) Int. Cl.
- *A62D 3/00* (2007.01)
- *C12P 5/00* (2006.01)
- *C12N 1/12* (2006.01)
- *C10G 1/00* (2006.01)
- *C10G 1/06* (2006.01)
- *C10G 32/00* (2006.01)
- *C12M 3/00* (2006.01)
- *B01D 53/14* (2006.01)
- *C07C 27/00* (2006.01)

(52) U.S. Cl. ............ 435/262.5; 208/400; 208/414; 423/220; 518/700; 435/166; 435/257.1; 435/281; 435/292.1

(58) Field of Classification Search .............. None
See application file for complete search history.

(56) References Cited

U.S. PATENT DOCUMENTS

| | | | |
|---|---|---|---|
| 2,793,219 A | 5/1957 | Barrett et al. |
| 2,955,122 A | 10/1960 | Whitaker |
| 5,326,164 A | 7/1994 | Logan |
| 5,666,800 A | 9/1997 | Sorensen et al. |
| 5,968,465 A | 10/1999 | Koveal et al. |
| 6,284,807 B1 | 9/2001 | Leviness et al. |
| 6,287,852 B1 | 9/2001 | Kondo et al. |
| 6,337,010 B1 | 1/2002 | Hofer |

(Continued)

FOREIGN PATENT DOCUMENTS

CA     2499264     4/2004

(Continued)

OTHER PUBLICATIONS

NRG Energy "NRG Energy Testing GreenFuel Technologies Algae Bioreactor System to Recycle Carbon Dioxide Emissions into Renewable Biofuels at Louisiana Power Plant" NRG News Release <http://phx.corporate-ir.net/phoenix.zhtml?c=121544&p=irol-newsArticle_Print&ID=984716&highlight=>, Apr. 13, 2007, 2 pages.*

(Continued)

*Primary Examiner* — Chris R Tate
*Assistant Examiner* — Aaron Kosar
(74) *Attorney, Agent, or Firm* — Edward T. Mickelson

(57) ABSTRACT

The present invention is generally directed to processes that integrate $CO_2$-producing conversions of hydrocarbonaceous assets with biofuels processes that utilize $CO_2$ photosynthesis. In some embodiments such processes involve the absorption of $CO_2$ in an absorption liquid. In some such embodiments such absorption is carried out in an absorption tower. In some other such embodiments, there is a subsequent desorption of the $CO_2$. Generally, at least some of the $CO_2$ captured by the absorption liquid is used to grow microbes or diatom species.

26 Claims, 3 Drawing Sheets

U.S. PATENT DOCUMENTS

| | | |
|---|---|---|
| 6,605,206 B1 | 8/2003 | Johnson et al. |
| 6,620,091 B1 | 9/2003 | Zavell et al. |
| 6,627,779 B2 | 9/2003 | O'Rear |
| 6,667,347 B2 | 12/2003 | O'Rear et al. |
| 6,686,511 B2 | 2/2004 | Miller et al. |
| 6,698,515 B2 | 3/2004 | Karanikas et al. |
| 6,702,937 B2 | 3/2004 | Johnson et al. |
| 6,703,429 B2 | 3/2004 | O'Rear et al. |
| 6,703,535 B2 | 3/2004 | Johnson et al. |
| 6,706,936 B2 | 3/2004 | O'Rear et al. |
| 6,720,359 B2 | 4/2004 | O'Rear et al. |
| 6,723,756 B2 | 4/2004 | Munson et al. |
| 6,773,578 B1 | 8/2004 | O'Rear et al. |
| 6,806,237 B2 | 10/2004 | O'Rear |
| 6,833,065 B2 | 12/2004 | O'Rear |
| 6,841,711 B2 | 1/2005 | Krug et al. |
| 6,846,402 B2 | 1/2005 | Hemighaus et al. |
| 7,018,525 B2 | 3/2006 | Miller et al. |
| 2004/0068150 A1 | 4/2004 | Johnson et al. |
| 2004/0230085 A1 | 11/2004 | Jakkula et al. |
| 2004/0256286 A1 | 12/2004 | Miller et al. |
| 2004/0256287 A1 | 12/2004 | Miller et al. |
| 2005/0064577 A1 | 3/2005 | Berzin |
| 2005/0077208 A1 | 4/2005 | Miller et al. |
| 2005/0239182 A1 | 10/2005 | Berzin |
| 2005/0260553 A1 | 11/2005 | Berzin |
| 2007/0048859 A1 | 3/2007 | Sears |

FOREIGN PATENT DOCUMENTS

| | | |
|---|---|---|
| JP | 3169324 | 7/1991 |
| JP | 10057745 | 3/1998 |
| JP | 10057745 A * | 3/1998 |
| WO | WO 9711154 | 3/1997 |
| WO | WO 03024604 | 3/2003 |
| WO | WO 03094598 A1 * | 11/2003 |
| WO | WO 03106346 | 12/2003 |
| WO | WO 03106349 | 12/2003 |
| WO | WO 03106351 | 12/2003 |
| WO | WO 03106353 | 12/2003 |
| WO | WO 03106354 | 12/2003 |
| WO | WO 2004028667 A1 * | 4/2004 |
| WO | WO 2005013671 | 2/2005 |
| WO | WO 2006108532 | 10/2006 |
| WO | WO 2007070452 | 6/2007 |

OTHER PUBLICATIONS

Sun, X. and Hobbs, R. "Power Plant Emissions to Biofuels" NREL-AFOSR Workshop on Algal Oil for Jet Fuel Production, Feb. 19-21, 2008, 28 pages.*

MIT "Cogen plant wins environmental award" MIT News, <http://web.mit.edu/newsoffice/2002/vestaward-1030.html>, Oct. 30, 2002, 2 pages.*

Wright, Sarah H. "Up on the Roof, Algae Appetites May Transform Waste into Energy" MIT News, <http://web.mit.edu/newsoffice/2004/algae.html>, Aug. 9, 2004, 2 pages.*

Kosaric, N. et al "Ethanol Production by Fermentation: An Alternative Liquid Fuel" Advances in Applied Microbiology, 1980, vol. 26, pp. 147-227.*

Sheehan, et al., "A Look Back at the U.S. Department of Energy's Aquatic Species Program: Biodiesel from Algate," National Renewable Energy Laboratory, NREL/TP-580-24190, pp. 245-246.

Shreve, R.N., *Chemical Process Industries*, 3rd edition, New York, McGraw-Hill, 1967, pp. 555-559.

* cited by examiner

PROCESS FOR INTEGRATING CONVERSION OF HYDROCARBONACEOUS ASSETS AND PHOTOBIOFUELS PRODUCTION USING AN ABSORPTION TOWER

FIELD OF THE INVENTION

This invention relates generally to biofuels production, and specifically to methods for harnessing carbon dioxide ($CO_2$) produced during hydrocarbonaceous asset conversion, and using said $CO_2$ to support photosynthesis in a biofuels precursor.

BACKGROUND

Carbon dioxide ($CO_2$) is a well-known greenhouse gas and attempts to reduce the emissions of this gas into the atmosphere are desirable. $CO_2$ is commonly formed when hydrocarbonaceous assets are converted into hydrocarbonaceous products, e.g., hydrogen or power. As an example, a gas-to-liquids (GTL) process converts roughly two-thirds of the starting gas (methane or natural gas) into hydrocarbonaceous liquid products with the other one-third being emitted as $CO_2$. The current high costs associated with capturing and sequestering this $CO_2$ using conventional amine scrubbing technology coupled with sequestration of high pressure $CO_2$ are such that doing so is generally not economically-viable. Accordingly, it is desirable to reduce both $CO_2$ emissions and the costs associated with their sequestration. Toward this end, it has been proposed that $CO_2$ be captured when electrical power is generated from hydrocarbonaceous assets, as for example in the integrated-gasification-combined-cycle (IGCC) process. See, e.g., U.S. Pat. No. 5,666,800.

Methods to capture and mitigate the entrance of $CO_2$ into the atmosphere have primarily focused on amine scrubbing from flue gas or super-atmospheric gas streams coupled with compression of the $CO_2$ prior to sequestration underground. This presents problems. First, the costs to compress the $CO_2$ can be significant. Second, there are questions as to whether or not the $CO_2$ sequestered in underground reservoirs will, in fact, remain there.

one approach to reduce greenhouse gas emissions is to substitute a crop-based biofuel for a petroleum-derived fuel. In preparing the crop-based biofuel, $CO_2$ is consumed during the plant growth cycle. For example, there is interest in ethanol production from corn, and biodiesel from various grains. The problems with this crop-based approach include: (1) diversion of scarce farmland that is engaged in growing food for manufacture of transportation fuels; (2) use of scarce fresh water for the production of biofuels (in the United States, the decline of the Ogallala aquifer due to agricultural use could restrict future agriculture); and (3) the energy used to create the finished biofuel (i.e., product) reduces the net energy production, wherein associated energy utilization steps include fertilization, planting, harvesting, drying, milling, fermenting, extracting, distilling, transesterification and the like (some studies have indicated that there is no net energy production from ethanol).

An alternative to crop-based biofuels is to use a photobiofuels process which converts the $CO_2$ into liquid hydrocarbonaceous products by use of photosynthetically-responsive microbes ("microbes"). A photobiofuels process, in the context of this invention, is a biological process employing microorganisms such as algae (e.g., microalgae) and/or diatoms (e.g., phytoplankton) to convert carbon dioxide into liquid hydrocarbonaceous products such as triglycerides, alcohols, acids, mono-esters and other oxygenated compounds. In doing this, the photobiofuels process uses sunlight as an energy source to produce lipids (triglycerides) and carbohydrates (e.g., sugars and starches). The photobiofuels process can also produce oxygen as a by-product. Photobiofuels processes can be characterized as open or closed, as described below.

An open photobiofuels process is one in which an aqueous liquid containing the algae and/or diatoms is in direct contact with the atmosphere. This is typically done using ponds. An advantage of an open photobiofuels process is its relatively low cost. Disadvantages include an inability to collect the produced $O_2$, an inability to prevent contamination of the aqueous liquid with native microbes, and difficulty in controlling the temperature. An excellent example of a photobiofuels process can be found in "A Look Back at the U.S. Department of Energy's Aquatic Species Program: Biodiesel from Algae" by Sheehan et al. (referred to herein as the "Sheehan report" or simply "Sheehan"). This document was prepared by the National Renewable Energy Laboratory as NREL/TP-580-24190.

A closed photobiofuels process is one in which the aqueous liquid containing the algae and/or diatoms is not in direct contact with the atmosphere, but is instead protected by a transparent structure which permits light to enter. Advantages of the closed photobiofuels process include the ability to collect produced $O_2$, protection of the liquid from introduction of native microbes, and improved ability to control the temperature. The primary disadvantage of this process is cost (see Sheehan, Technical Review pages 245-246). Examples of closed photobiofuels processes can be found in the following U.S. Patent Application Publications by Berzin: US20050260553, US20050239182, and US20050064577—collectively referred to herein as the "Berzin patents" or simply "Berzin".

Looking at the open photobiofuels process described in Sheehan, several attractive features have been discovered: (1) $CO_2$ from coal-fired power plants can be converted into a photobiofuel (Executive Summary, page i); (2) the $CO_2$ from the coal-plants was a 13% concentration and bubbled into ponds containing the microbes (Program summary page 4); (3) concentrated, high pressure $CO_2$ sources in power plants, synthetic fuels plants, and IGCC plants were found to be the most economical sources (Technical Review, page 216); (4) >90% of injected $CO_2$ is consumed (Executive Summary, page ii); (5) the process does not use fresh water, but rather uses more abundant saline water that cannot be used in conventional agriculture (Program Summary, page 10); (6) the yield per acre of biofuel is thirty times that which can be obtained for crop-based biofuels (Program Summary, page 3); (7) the resulting algae can contain 60 wt % triglycerides—a photobiofuel pre-cursor (Program Summary, page 6); (8) oxygen is made as a by-product, but this can act to inhibit microbe growth (Technical Review, page 181); (9) the reagents needed to support growth of the microbe (minerals and nitrogen) can be recycled (Technical Review, page 145); (10) methane or ethanol can be produced from fermentation of biomass that does not yield triglycerides (Program Summary, page 6); and (11) the triglycerides can also be used as valuable specialty chemicals (Technical Review, page 1).

Despite its attractiveness, several problems have been identified or associated with the above-described open photobiofuels process: (1) the microbes may only grow well under rather narrow conditions of salinity, pH, and temperature (Technical Review, page 16); (2) low nighttime temperatures can limit productivity (Executive Summary, page ii); (3) yearly temperature cycles (growing season) can also limit productivity (Technical Review, page 213); (4) zooplankton can act as grazers and eat the microbes which generate the photobiofuel (Technical Review page 152), and such grazers can be, a particular problem at night (Technical Review, page 180); (5) carbon dioxide is only consumed during the day when sunlight is available; (6) the cost of the produced biodiesel was estimated (in 1995 dollars) as being between $1.40 to $4.40/gallon; and even with carbon credits, this was judged to be twice the cost of petroleum diesel, and therefore not competitive (Program Summary, page 19; and Executive Summary, page ii); (7) an analysis in the report concluded, that it will be difficult to find many locations where all the resources required for microalgae cultivation (e.g., flatland, brackish or waste waters, and low cost $CO_2$ supplies) are all available in juxtaposition (Technical Review, page 259).

One approach to improve upon the economics of such above-described processes is to use a closed photobiofuels process. This affords a better chance to control the temperature, salinity, pH and microbial species. Examples of this are shown the Berzin patents. However, am economic analysis of closed systems performed by Sheehan concluded that the costs of these systems were prohibitive (Program Summary, page 5)

While the price of petroleum diesel has increased markedly since the above described 1995 study and might now make this viable, efforts to improve the economics of such photobiofuels process are still desirable. The approach taken herein to improve such economics is to enhance the integration of the processes for conversion of hydrocarbonaceous assets and the photobiofuels process. Improved economics are achieved either by lower cost operations, improved productivity, improved value of the product, and combinations thereof.

BRIEF DESCRIPTION OF THE INVENTION

The present invention is generally directed to processes that integrate $CO_2$-producing conversions of hydrocarbonaceous assets with biofuels processes that utilize $CO_2$ in photosynthesis. In some embodiments, such processes involve the absorption of $CO_2$ in an absorption liquid. In some such embodiments, such absorption is carried out in an absorption tower. In some or other such embodiments, there is a subsequent desorption of the $CO_2$. Generally, at least some of the $CO_2$ captured by the absorption liquid is used to grow microbes or diatom species.

In some embodiments, the present invention is directed to an integrated process for conversion of hydrocarbonaceous assets, the process comprising the steps of: (1) converting hydrocarbonaceous assets to generate a first super-atmospheric pressure $CO_2$-containing gas; (2) absorbing at least a portion of the $CO_2$ from the first super-atmospheric pressure $CO_2$-containing gas, the absorbing being done at a first temperature and with an absorption liquid; (3) desorbing at least a portion of the absorbed $CO_2$ at a second temperature to form a second super-atmospheric pressure $CO_2$-containing gas, wherein the second temperature is higher than the first temperature, and the concentration of $CO_2$ in the second super-atmospheric pressure $CO_2$-containing gas is higher than the concentration of $CO_2$ in the first super-atmospheric pressure $CO_2$-containing gas; and (4) using at least a portion off the $CO_2$ in the second super-atmospheric pressure $CO_2$-containing gas to support photosynthesis in a photobiofuels process.

In some alternate embodiments, the present invention is directed to an integrated process for conversion of hydrocarbonaceous assets, the process comprising the steps of: (1) converting hydrocarbonaceous assets to produces a $CO_2$ containing gas; (2) absorbing at least a portion of the $CO_2$ of the $CO_2$-containing gas into an absorption liquid in an absorption tower, wherein the absorption liquid flows downward, and wherein the $CO_2$-containing gas flows upward; and (3) using at least a portion of the $CO_2$ in the absorption liquid to support photosynthesis in a photobiofuels process. In some such embodiments, the process may further comprise the steps of: (i) forming biomass in the absorption liquid used in the photobiofuels process; (ii) removing the biomass to form a regenerated absorption liquid; and (iii) recycling at least a portion of the regenerated absorption liquid to the absorption tower.

In some of the above-described embodiments, the photobiofuels process involves harvesting of microalgae, and the corresponding processes can further comprise a step of regulating microalgae metabolism at night, wherein said regulation can involve a method such as, but not limited to, (a) temperature modulation; (b) salinity modulation; (c) pH modulation; (d) modulation of $O_2$ concentration, and (e) combinations thereof.

In some of the above-described embodiments, the processes can further comprise the production of 0, in the photobiofuels process and use of at least a portion of this $O_2$ to convert the hydrocarbonaceous assets, wherein use of the $O_2$ is typically as a gaseous oxidant for synthesis gas production and/or an oxidant of synthesis gas to produce power, and wherein the photobiofuels process is typically a closed photobiofuels process.

In some of the above-described embodiments, energy is created during the converting of hydrocarbonaceous assets, wherein said energy typically manifests itself in a form such as, but not limited to, electrical power, stream, hot gases, super-atmospheric pressure gases, and combinations thereof; and wherein at least a portion of this energy is typically utilized in the photobiofuels process in a manner such as, but not limited to, stirring and pumping the liquid in the photobiofuels process, sonicating the liquid, processing the liquid in a high shear mixer, separating microalgae contained therein from the liquid, drying microalgae contained therein, grinding microalgae contained therein to free lipids and other components, separating the components, and the like.

In some of the above-described embodiments, the processes further comprise producing a methylester for use as a biodiesel, the producing comprising the substeps of: (a) recovering trigylcerides from the photobiofuels process; (b) transesterifying the trigylcerides from the photobiofuels process with an alcohol to form an ester and glycerin; and (c) purifying the ester; wherein at least a portion of the alcohol used in the transesterification is manufactured, in the process for converting hydrocarbonaceous assets, by synthesis gas conversion processes such as, but not limited to, methanol synthesis. Fisher-Tropsch, and the like.

In some of the above-described embodiments, the processes further comprise the steps of (a) removing a reduced nitrogen species from the $CO_2$-containing gas derived from the converting of hydrocarbonaceous assets; and (b) consuming the reduced nitrogen species in the photobiofuels process.

In some of the above-described process embodiments, the step of converting the hydrocarbonaceous assets involves a Fischer-Tropsch process, and wherein said process further comprises the steps of (a) recovering triglycerides from the photobiofuels process; (b) recovering a product from the Fischer-Tropsch process; (c) processing at least a portion of both the triglyceride and the Fisher-Tropsch product in a hydroprocessing process to form paraffinic liquid hydrocarbonaceous products, and (d) recovering at least a portion of the paraffinic liquid hydrocarbonaceous products.

In some of the above-described embodiments, the processes further comprise the steps of: (a) recovering triglycerides from the photobiofuels process; (b) converting the triglycerides to fatty acids, at least a portion of which are unsaturated; (c) oligomerizing the unsaturated fatty acids to form polyacids; and (d) esterifying the polyacids with an alcohol to form an unsaturated polyester operable for use as a synthetic lubricant.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

Figure 1:
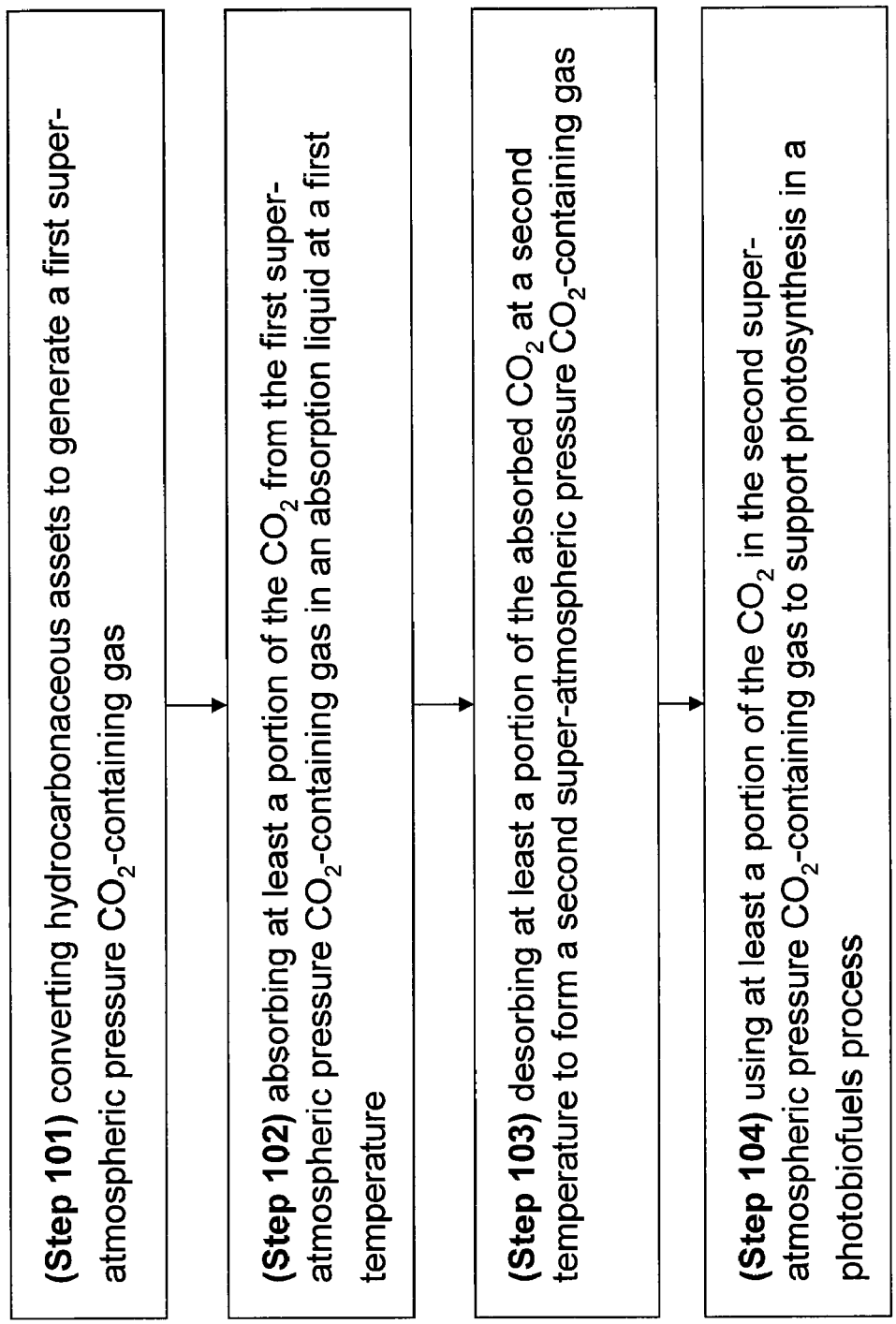
FIG. 1 depicts, in stepwise fashion, a process for integrating $CO_2$-producing conversions of hydrocarbonaceous assets with biofuels processes that utilize $CO_2$ for photosynthesis, in accordance with some embodiments of the present invention.

The present invention is generally directed to processes that integrate $CO_2$-producing conversions of hydrocarbonaceous assets with biofuels processes that utilize $CO_2$ in photosynthesis, i.e., photobiofuels processes. In some embodiments, such processes involve the absorption of $CO_2$ in an absorption liquid. In some such embodiments, such absorption is carried out in an absorption tower. In some other such embodiments, there is a subsequent desorption of the $CO_2$. Generally, at least some of the $CO_2$ captured by the absorption liquid is used to grow microbes or diatom species.

1. DEFINITIONS

Certain terms and phrases are defined throughout this description as they are first used, while certain other terms used in this description are defined below:

"Processes for conversion of hydrocarbonaceous assets" are processes that first convert a hydrocarbonaceous asset to synthesis gas (via a synthesis gas generation process) and then convert the synthesis gas into a fuels process (via a synthesis gas conversion process). The processes for conversion of hydrocarbonaceous assets contain a super-atmospheric pressure $CO_2$-containing gas stream which is more suitable for extraction of $CO_2$ than is an atmospheric gas stream (such as flue gas).

"Synthesis gas" or "syngas" is a mixture containing carbon monoxide and hydrogen and optionally other gases such as water and carbon dioxide. Because catalysts used in the synthesis gas conversion process are poisoned by additional species, such as sulfur and nitrogen compounds, these should be kept as low as possible in the feed directed to that process.

The term "super-atmospheric" refers to pressures in excess of 14.7 psia. For example, greater than or equal to 50 psig, or 100 psig, or 200 psig.

"Caustic water" is water with a pH greater than 7 for example greater than or equal to 8 or greater than or equal to 9, or greater than or equal to 10. The pH is measured when the water is exposed to the atmosphere and not when exposed to additional $CO_2$ beyond that normally found in the atmosphere. The pH is elevated by the presence of Group I and/or Group II ions, e.g., sodium and potassium. Ions which form insoluble precipitates in the presence of $CO_2$ (e.g., calcium and magnesium) are not preferred. If ions that form insoluble precipitates are present, they can be removed by exposing the caustic water to $CO_2$ and removing the precipitate, or they can be removed by ion exchange. Sources of caustic water can be non-caustic water to which these ions are added (in the form of salts), sea water, or natural brines. Caustic water is essentially free of amines that might otherwise be used to adsorb $CO_2$. While amines can be used to adsorb $CO_2$ from super-atmospheric pressure gas streams, they pose a potential aqueous pollution hazard and can be toxic to algae when used to adsorb $CO_2$ from atmospheric pressure systems envisioned in this application.

"Hydrocarbonaceous" refers to a solid, liquid or gas containing carbon and hydrogen and optionally other elements.

"Hydrocarbonaceous assets" are materials comprising the elements H and C, and optionally S, N, O, and other elements used to manufacture hydrocarbonaceous products. Examples of such assets include natural gas, methane, coal, petroleum, petroleum coke, tar sands, bitumen, oil emulsions, oils shale, shale oil, waste plastics, waste tires municipal waste, derivatives of these, and their combinations and/or mixtures.

"Hydrocarbonaceous products" are a pure compound or mixtures of compounds comprising H and C, and optionally S, N, O, and other elements. Examples include gasoline, jet fuel, diesel fuel, lubricant base oil, alcohols such as methanol and ethanol, etc.

"Paraffinic liquid hydrocarbonaceous products" are products that contain more than 50% paraffins, for example, more than 75% or more than 90%. Examples of these include naphtha, lubricant base oils, and transportation fuels (e.g., jet fuel and diesel fuel).

A "synthesis gas-generation process" is one that converts a hydrocarbonaceous asset into synthesis gas (syngas) by use off a gaseous oxidant. The gaseous oxidant can be purified $O_2$, enriched air, air, steam, carbon dioxide, and combinations thereof. The process can either be carried out above-ground or in situ. Examples of above ground synthesis gas generation processes that use gaseous hydrocarbons having carbons numbers less than 20 (e.g., methane) as feedstocks for the reactor include auto-thermal reformer (ATR), partial oxidation (POX), gas heater reformer (GHR), and steam reforming. When these feedstocks contain more than 2 mol % $C_2$ and heavier hydrocarbons, a pre-converter (pre-reformer) is often used to convert the $C_2$ and higher hydrocarbons into methane. The pre-reformer uses a catalyst containing a Group VIII metal catalyst (e.g., Ni) with hydrogen at super-atmospheric pressures. Synthesis gas can also be generated by reacting underground hydrocarbonaceous assets with a gaseous oxidant. An example of such an in situ process is described in U.S. Pat. No. 6,698,515, issued Mar. 2, 2004 to Karanikas et al. Examples of underground hydrocarbonaceous assets include coal, oil shale, heavy oil, tar sands, petroleum deposits, and bitumen. An example of a petroleum deposit suitable for in situ conversion is a petroleum deposit from which easily-extractable petroleum has been extracted by conventional methods such as piping, steam flooding, and water flooding.

A "synthesis gas conversion process" is one that converts synthesis gas into a hydrocarbonaceous product, hydrogen, electrical power, or combinations thereof. Hydrocarbonaceous products include materials that are liquid or solid at 20° C. and ambient pressure that contain carbon, hydrogen, and optionally oxygen. Examples of hydrocarbonaceous products include naphtha, diesel, jet fuel distillate fuel, solvents, and base oils. Methanol is another example of a hydrocarbonaceous product. The syngas conversion process that makes a hydrocarbonaceous product can be a Fischer-Tropsch synthesis process, a methanol synthesis process, a dual-functional syngas conversion process, or a gas-to-olefins (GTO) process. The GTO process couples a methanol synthesis process with a methanol-to-olefins (MTO) process and makes ethylene, propylene, and/or combinations thereof. The synthesis gas can also be converted into hydrogen by reacting the carbon monoxide with water to form $CO_2$ and $H_2$ via the water-gas shift reaction. Power can be generated from the synthesis gas by burning it or by burning hydrogen that is produced from the synthesis gas. An example of a process that produces synthesis gas and burns it to form power is the integrated gasification, combined-cycle (IGCC) process mentioned previously. Examples of the Fisher-Tropsch process are described in U.S. Pat. No. 6,846,402. An example of a dual-functional syngas conversion process can be found in U.S. Pat. No. 6,703,429 and references cited therein.

"Reduced nitrogen species" are nitrogen species that are gases under ambient conditions and do not contain oxygen. Examples are ammonia and cyanides. Reduced nitrogen species can be used by the microorganisms (microbes) as a nutrient.

A "photobiofuels process," as defined herein, is a biological process employing microorganism(s) such as algae and/or diatoms to convert carbon dioxide into liquid hydrocarbonaceous products such as triglycerides, alcohols, acids, monoesters and other oxygenated compounds—via a photosynthetic route. The microbes are typically in an aqueous liquid (such as water or caustic water). In doing this, the photobiofuels process uses sunlight as an energy source to produce lipids (e.g., triglycerides) and carbohydrates (e.g., sugars and starches). The photobiofuels process can also produce oxygen as a by-product. Assuming that the product is a triglyceride composed of saturated $C_{16}$ acid, am overall stoichiometry would be:

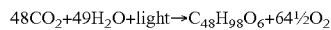

$$48CO_2+49H_2O+light \rightarrow C_{48}H_{98}O_6+64\tfrac{1}{2}O_2$$

Photobiofuels processes can be characterized as open and closed, as described in greater detail below.

An "open photobiofuels process" is one in which an aqueous liquid containing the algae and/or diatoms is in direct contact with the atmosphere. This is typically done using ponds. An advantage of an open photobiofuels process is its low cost. Disadvantages include an inability to collect the produced $O_2$, an inability to prevent contamination of the aqueous liquid with native microbes, and difficulty in controlling the temperature.

A "closed photobiofuels process" is one in which the aqueous liquid containing the algae and/or diatoms is not in direct contact with the atmosphere, but is instead protected by a structure, at least a portion of which is transparent, and which permits light to enter. Advantages of the closed photobiofuels process include the ability to collect produced $O_2$, protection of the liquid from introduction of native microbes, and an improved ability to control the temperature. The primary disadvantage of this process is cost (see Sheehan, Technical Review pages 245-246). Examples of a closed photobiofuels process can be found in U.S. Patent Application Publications by Berzin (US20050260553, US20050239182, and US20050064577).

"Hydroprocessing" refers to a collection of processes that react a hydrocarbonaceous liquid with hydrogen under pressure with a catalyst. The collection of such processes include, but are not limited to, hydrotreating, hydrocracking, hydroisomerization, and hydrodewaxing.

2. SCOPE OF THE INVENTION

As mentioned above, it is desirable to improve upon the economics of processes that integrate conversion of hydrocarbonaceous assets with photobiofuels processes. The approach described herein will focus on improving such economics by enhancing the integration of the corresponding sub-processes.

As indicated by the economic study in Sheehan, the source of the $CO_2$ can play a key role in the economics of the overall system. Lowest costs were seen when amine scrubbers were used to extract the $CO_2$ from concentrated, high pressure $CO_2$ sources in power plants, synthetic fuels plants, and IGCC plants rather than from dilute (13%) low pressure flue gas (Technical Review, page 216). The costs to "capture" this $CO_2$ can dominate the overall economics and these costs can be minimized when the $CO_2$ source is concentrated and at super-atmospheric pressure.

Capturing $CO_2$ by conventional amine scrubbing from a high pressure source involves mixing the $CO_2$-containing gas stream with an amine absorption solution in a scrubber, withdrawing the $CO_2$-rich amine absorption solution, and freeing the $CO_2$ from the amine absorption solution by reducing pressure. This is commonly known as the pressure-swing absorption process. This results in a low-pressure $CO_2$ gas which must be compressed in order to be processed in the photobiofuels process. The costs to re-compress the $CO_2$ can be significant. In order to avoid these re-compression costs, the $CO_2$ can be freed from the absorption solution by raising the temperature so as to produce a super-atmospheric $CO_2$ stream—this is known as a temperature-swing absorption process. However, amines can decompose when heated at temperatures sufficient to remove the $CO_2$. When amine decomposition is a problem (as it is when the synthesis gas conversion process is a Fischer-Tropsch or methanol synthesis process), it is preferable that the absorption solution does not contain amine, but rather is an aqueous absorption solution (e.g., water or a caustic water).

When $CO_2$ is captured from an atmospheric pressure flue gas, removing the $CO_2$ from the absorption solution by reducing pressure is generally not practical. The only practical solution is to increase temperature, and as noted, this increases the likelihood of amine decomposition. When the amine decomposes, it increases the costs, and creates a pollution problem from the decomposed amine. Accordingly, aqueous absorption solutions operated in a temperature-swing process should result in lower costs to capture the $CO_2$. See, e.g. U.S. Pat. Nos. 6,723,756; 6,720,359; 6,667,347; and 6,620,091 for applications of a temperature-swing absorption process using an aqueous absorption solution with a gas-to-liquids process, where the $CO_2$ is compressed and sequestered underground.

Another approach to capturing the $CO_2$ is by directly adsorbing it in an absorption liquid, e.g., water or caustic water, and then introducing microbes into this $CO_2$-containing solution for use in a photobiofuels process. The conventional process schemes described in Sheehan involve either recovery of the $CO_2$ from a flue gas in the form of a gas, or injecting the flue gas stream directly into the photobiofuels reactor. Handling this volume of gas will require large and expensive equipment and will likely result in a back-pressure on the upstream processes for conversion of hydrocarbonaceous assets—this will reduce its efficiency. An improvement is the use of a simple absorption tower on the flue gas; but rather than desorbing the $CO_2$ from the absorption liquid, the liquid is used in the photobiofuels process to convert the absorbed $O_2$. Absorption systems of this type (commonly called scrubbers) are used in power plants to control $SO_x$ emissions. Such absorption towers can be designed with low pressure drop. The absorption liquid flows downward and the gas flows upward. After the microbes have consumed the $CO_2$ in the absorption liquid, they can be removed/separated from the absorption liquid, and the absorption liquid can be recycled back to the absorption tower (vide infra). It is important to remove a majority of the microbes and biomass from the absorption liquid because these will accumulate in the absorption tower (referred to as fouling).

As noted in the economic analysis of Sheehan water sources can limit the sites where photobiofuels reactors can be used. While caustic water sources are more abundant than fresh water, their sources are not unlimited—especially for inland locations. Likewise, an examination of the stoichiometry for the conversion of $CO_2$ into lipids shows that considerable water is consumed in the conversion. Lastly, water will invariably be lost by evaporation. Accordingly, a supply of water will be needed.

In many processes for conversion of hydrocarbonaceous assets water is formed as a by-product. For example, when a Fischer-Tropsch process is used as the synthesis gas conversion process in converting hydrocarbonaceous assets, more pounds of water are produced than pounds of hydrocarbonaceous product. At least a portion of this water produced in the processes for conversion of hydrocarbonaceous assets can be used in the photobiofuels process. This water is produced from synthesis gas and contains no ions to promote an increase in pH. It may, however, contain some acids, alcohols, oxygenates and hydrocarbons. These can be removed by oxidation, distillation, or reaction with microbes (such as a biooxidation pond, or a photobiofuels reactor). Examples of how to treat water from a Fischer-Tropsch process can be found in the following International (PCT) Patent Application Publications: WO2003106354A1, WO2003106346A1, WO2003106353A1, WO2003106351A1, and WO2003106349A1.

When caustic water is used in the photobiofuels process, and when water is consumed by reaction with microbes or evaporation, the pH will increase. The desired pH to absorb $CO_2$ in the $CO_2$-containing gas of the processes for conversion (i.e., the converting) of hydrocarbonaceous assets can be higher than the optimum pH for growth of microbes in the photobiofuels process. The pH in the liquid in the photobiofuels process can be regulated by controlling the blending of the water from the processes for conversion of hydrocarbonaceous assets, and by controlling the amount of $CO_2$ dissolved in the absorption liquid from the absorption tower. The amount of $CO_2$ in the absorption tower is in turn controlled by the ratio of absorption liquid to the $CO_2$-containing gas, the contact time in the absorption tower, the temperature of the absorption liquid, and combinations thereof.

The pH for optimum growth of microbes in the photobiofuels process may typically be over 6, for example, over 8, or over 9, or between 8 and 10. Additionally, the salinity can generally influence the growth of microbes with an optimum (measured as a conductivity) of less than 70 mmho·cm$^{-1}$, for example, between 5 mmho·cm$^{-1}$ and 50 mmho·cm$^{-1}$, or between 10 mmho·cm$^{-1}$ and 30 mmho·cm$^{-1}$. The salinity of the photobiofuels process can be controlled by blending the water from the processes for conversion of hydrocarbonaceous assets. Control of the blending of the water from the processes for conversion of hydrocarbonaceous assets impacts both salinity and pH, while control of the amount of dissolved $CO_2$ primarily impacts the pH. Thus, these two controls can be used in combination to produce optimal conditions for microbe growth.

In some cases, temperature can influence the growth of microbes, and cold temperatures at night and during winter can decrease productivity. The target temperatures for the photobiofuels reactor are typically between 10° C. and 40° C., for example, between 20° C. and 35° C. Processes for conversion of hydrocarbonaceous assets frequently generate heat energy in the form of steam (a gas), or hot condensate from steam (a liquid). These hot gases and liquids will have temperatures above 30° C., for example, above 40° C., and can be used to regulate the temperature of the photobiofuels reactor. Likewise, during hot summer days, the temperature of the photobiofuels reactor can exceed the target temperature. Processes for conversion of hydrocarbonaceous assets frequently generate cold gases and liquids in the form of cold nitrogen gas from an air separations unit or chilled water that is prepared in the air separations unit. These cold gases and liquids will have temperatures below 40° C., for example below 30° C. or below 20° C. The hot and cold gases and liquids can be introduced into the photobiofuels reactor in tubes designed to promote heat exchange, or they can be directly injected into the liquid in the photobiofuels reactor.

In some cases, it can also be valuable to define a secondary target for pH, salinity, and/or temperature and from time to time adjust the conditions of the photobiofuels process to this secondary target. Operation at the secondary target can be desirable as a method of controlling grazers. Also at night, the microbes do not perform photosynthesis, and instead use the reverse of the process to provide energy for their metabolism. So at night, it can be desirable to suppress the metabolism of the microbes to prevent the consumption of the triglycerides and carbohydrates formed during the day. The temperature for the secondary target should be between 0° C. and 70° C., the salinity for the secondary target should be less than 100 mmho·cm$^{-1}$, and the pH1 for the secondary target should be greater than 5. Another way to suppress metabolism at night is to remove the $O_2$ which is needed for this reaction.

Since by its very nature a photobiofuels process only converts $CO_2$ during the daytime, $CO_2$ produced in the processes for conversion of hydrocarbonaceous assets at night cannot be converted at night. In order to improve the overall conversion of $CO_2$, the $CO_2$ produced in the processes for conversion of hydrocarbonaceous assets can be stored and then processed in the photobiofuels process during the day. Means for storing the $CO_2$ during the night include storing it as a super-atmospheric pressure gas in underground salt domes, storing it as a super-atmospheric pressure gas in above ground gas tanks, and storing it as $CO_2$ dissolved in caustic water, e.g., in a tank.

As noted in Sheehan, $O_2$ produced as a byproduct in the photobiofuels reactor can inhibit the growth of the microbes (Technical Review page 181). $O_2$ is frequently needed in the processes for conversion of hydrocarbonaceous assets. For example when the synthesis gas generation process in processes for conversion of hydrocarbonaceous assets uses $O_2$ or enriched air as a gaseous oxidant, at least a portion of this demand can be supplied by the $O_2$ from a closed photobiofuels reactor. Likewise, when the synthesis gas conversion process generated power by the combustion of the synthesis gas, $O_2$ or enriched air can be of use. When air is used in this combustion process $NO_x$ can be formed. Use of $O_2$ or $O_2/CO_2$ mixtures can prevent this. The $O_2$ from the closed photobiofuels reactor can be recovered by sparging the liquid in the photobiofuels reactor with gaseous $CO_2$. This has the desired effect of introducing $CO_2$ into the liquid and removing excess $O_2$. The $O_2$ in the sparged gas can be separated from $CO_2$ by scrubbing the $O_2/CO_2$ mixture with water or caustic water. Alternatively, the mixture can be used directly as the oxidant when the synthesis gas is burned to make power and a $CO_2$-containing flue gas. $CO_2$ remaining in the flue gas can be recycled to the closed photobiofuels reactor as described above.

$O_2$ is only produced during daytime hours (via photosynthesis), while the processes for conversion of hydrocarbonaceous assets operate night and day. Thus, the $O_2$ from the photobiofuels process can be used as a supplement during daytime operations. Alternatively, if continuous use is desired, a portion of the $O_2$ produced during the day can be stored using equipment described above for the storage of $CO_2$ and then recovered and used at night.

A cost component to the photobiofuels process is the power required, e.g., for stirring and pumping the liquid, separating the microbes from the liquid, drying the microbes, grinding the microbes to free the lipids and other components, and separating the components (e.g., lipids, carbohydrates, water, and residues). The processes for conversion of hydrocarbonaceous assets can produce energy in the form of electrical power, super-atmospheric pressure gases, hot gases (e.g. those with temperature above 40° C.), steam and combinations, and the like. Such produced energy can be used in the photobiofuels process for applications such as those described above.

As an alternative to processing dried microbes, microbes present in a liquid product from the photobiofuels process can be broken apart into components, and these components can be separated. Methods for breaking the microbes while in the liquid include high shear separation and sonication. Both require energy which can be provided by the processes for conversion of hydrocarbonaceous assets. The energy and frequency of the sonication device can be selected to break apart the microbes but not to break apart the sub-unit organelles which contain the separate components, for example liposomes. An example of sonication is can be found in U.S. Pat. No. 5,326,164.

Typically, triglycerides produced from the photobiofuel process cannot easily be used as such in a fuel because their viscosity is too high. Accordingly, in some such embodiments the triglycerides are converted into methyl esters by a chemical process called transesterification. Glycerin is a by-product from this reaction. An alcohol, such as methanol, is needed for the transesterification process. Alcohols can be made in the processes for conversion of hydrocarbonaceous assets, for example, the synthesis gas conversion process can be a methanol synthesis process. In these or other embodiments, the synthesis gas conversion process can be a Fischer-Tropsch process which produces methanol and higher alcohols, for example, ethanol, propanol, butanol, and pentanol. These can be recovered from the by-product water stream from this process. Examples of how to recover alcohols from this water stream can be found in the following PCT Patent Application Publications: WO2003106354A1, WO2003106346A1, WO2003106353A1, WO2003106351A1, and WO2003106349A1. Ethanol can also be produced by fermenting the carbohydrates produced by the microbes.

When the process for conversion of the hydrocarbonaceous asset uses a Fisher-Tropsch process to convert the synthesis gas, but after hydroprocessing, the resulting liquid hydrocarbonaceous products can contain few, if any, elements besides carbon and hydrogen. This can result in liquids that are highly non-polar and which, when used as fuels, will have well-known problems with lubricity. The lubricity of these fuels can be improved by blending in at least a portion of the methyl ester or triglyceride from the photobiofuels process.

One of the elements (i.e., nutrient) needed to support growth of the microbes is nitrogen, and supply of this element contributes to the overall economics. In order to be useful to microbes in the photobiofuels process, the nitrogen must be in some other form than inert $N_2$. While it has been suggested that $NO_x$ from flue gas could act to provide this nutrient (see Sheehan, Technical Review, page 241), another source of this nutrient is in the synthesis gas produced and consumed in the process for conversion of the hydrocarbonaceous asset. Unlike the $NO_x$ in flue gas, the nitrogen will be in the form of reduced nitrogen species $NH_3$ and HCN, such as is described in U.S. Pat. Nos. 5,968,465 and 6,284,807. It is desirable to remove these components from the synthesis gas as they can interfere with downstream conversion of the synthesis gas. Removing these reduced nitrogen species from the synthesis gas provides a way of improving the performance of the downstream synthesis gas process and providing a nutrient to the microbes in the photobiofuels process where the reduced nitrogen species are consumed.

In some embodiments, the products form the photobiofuels process can contain hydrocarbons that have poor cold climate properties (e.g., pour point, cloud point, cold filter plugging point, and freeze point). Likewise, the esters derived from triglycerides can have poor cold climate properties when used in some locations and purposes (for example, esters would not be acceptable in current jet fuels). Thus, as an alternative to transesterification, in some embodiments it can be desirable to convert the triglycerides by hydroprocessing processes to form paraffinic liquid hydrocarbonaceous products. An example of the use of hydroprocessing to convert these compounds into paraffinic liquid hydrocarbonaceous products is described in U.S. Patent Application Publication US20040230085. However, if the process for conversion of the hydrocarbonaceous assets includes a Fischer-Tropsch process, the products from the Fischer-Tropsch process will also need to be refined in a hydroprocessing process. The overall economics can be improved if both the triglycerides and the Fischer-Tropsch product are processed in the hydroprocessing process—either as a blend or in separate blocks.

In some cases, the economics of the photobiofuels process can be improved by manufacturing specialty products in addition to, or instead of, fuels. Examples include, but are not limited to, pigments, vitamins, or specialty chemicals. In some embodiments, the triglycerides contain significant quantities of unsaturated fatty acids which can be detrimental to the quality of ester fuels, so conversion of these compounds into esters for use as a fuel may face problems. The associated fuel-stability problems can be corrected by use of anti-oxidant additives. Alternatively, the unsaturated components can be converted to paraffinic liquid hydrocarbonaceous products when they are hydroprocessed. But the presence of the unsaturated groups offers another option of a high value product—the manufacture of biologically-based lubricants. The unsaturated fatty acids can be oligomerized to form a polyacid (e.g., an acid dimer or oligomer). This polyacid can then be converted with an alcohol into an unsaturated polyester by esterification as described above for transesterification. The unsaturated polyester can then be hydrogenated to form a saturated polyester. The alcohol can come from the same sources noted above in the manufacture of esters for use as biodiesel. Examples of processes for manufacturing fatty acids from trigylcerides can be found in R. N. Shreve, *Chemical Process Industries,* $3^{rd}$ edition, New York, McGraw-Hill, 1967, pp. 555-559. Examples of processes to oligomerize unsaturated fatty acids can be found in U.S. Pat. Nos. 2,793, 219 and 2,955,122. Alternatively, the acid dimer and/or oligomer can be hydrogenated to form a paraffinic hydrocarbonaceous product that will have a viscosity suitable for use as a lubricant base oil.

If a Fischer-Tropsch process is used to convert the synthesis gas in the processes for conversion of hydrocarbonaceous assets, the product(s) from this process can be used to make lubricant base oils. These base oils can be blended with ester or paraffinic lubricants from the photobiofuels process. Examples of the preparation of lubricant base oils from a Fischer-Tropsch process can be found in the following U.S. Pat. Nos. and Patent Publications: U.S. Pat. Nos. 6,337,010; 6,605,206; 6,627,779; 6,686,511; 6,702,937; 6,703,535; 6,706,936; 6,773,578; 6,806,237; 6,833,065; 6,841,711; 7,018,525; US20040068150; US20040256286; US20040256287; and US20050077208.

What follows is a discussion more specifically directed to such above-described integrated processes, wherein said processes comprise either a $CO_2$ desorption step or a $CO_2$ absorption tower.

3. INTEGRATED PROCESSES COMPRISING A DESORPTION STEP

As previously mentioned in some embodiments, the present invention is directed to processes that integrate $CO_2$-producing conversions of hydrocarbonaceous assets with biofuels processes that utilize $CO_2$ in photosynthesis, wherein such processes involve the absorption of $CO_2$ in an absorption liquid followed by a subsequent desorption of the $CO_2$ to grow photosynthetically-responsive microbes (e.g., microalgae).

Referring to the flow diagram of FIG. 1, in some embodiments, the present invention is directed to an integrated process for conversion of hydrocarbonaceous assets, the process comprising the steps of: (Step 101) converting hydrocarbonaceous assets to generate a first super-atmospheric pressure $CO_2$-containing gas; (Step 102) absorbing at least a portion of the $CO_2$ from the first super-atmospheric pressure $CO_2$-containing gas in an absorption liquid, the absorbing being done at a first temperature; (Step 103) desorbing at least a portion of the absorbed $CO_2$ at a second temperature to form a second super-atmospheric pressure $CO_2$-containing gas, wherein the second temperature is higher than the first temperature, and the concentration of $CO_2$ in the second super-atmospheric pressure $CO_2$-containing gas is higher than the concentration of $CO_2$ in the first super-atmospheric pressure $CO_2$-containing gas; and (Step 104) using at least a portion of the $CO_2$ in the second super-atmospheric pressure $CO_2$-containing gas to support photosynthesis in a photobiofuels process.

In some such above-described process embodiments, the absorption liquid is selected from the group consisting of water and caustic water. In some such embodiments, water is formed in the step of converting hydrocarbonaceous assets and at least a portion of this water can be blended with the absorption liquid.

In some such above-described process embodiments a target pH is set or established for the absorption liquid used in the photobiofuels process, and the pH to this target pH can be controlled by methods such as, but not limited to, (a) controlling blending of water from the converting of hydrocarbonaceous assets; (b) controlling temperature of the absorption liquid; (c) controlling absorption liquid to gas ratio; and (d) combinations thereof. In some such embodiments, the pH target is typically greater than 6, and more typically between 8 and 10.

In some such above-described process embodiments, a target salinity is established for the absorption liquid used in the photobiofuels reactor, and the salinity to this target can be controlled by a controlled blending of water from the converting of hydrocarbonaceous assets. In some such embodiments, the salinity is measured in terms of conductivity, wherein the conductivity is typically less than 70 mmho·cm$^{-1}$, and more typically between 10 mmho·cm$^{-1}$ and 30 mmho·cm$^{-1}$.

In some such above-described process embodiments, a target temperature is established for the photobiofuels process, and temperature to this target is controlled by use of gases and liquids from the converting of hydrocarbonaceous assets, said gases and liquids typically being selected from the group consisting of steam, condensate from steam, cold nitrogen gas, chilled water, and combinations thereof. In some such embodiments, the target temperature is typically between 10° C. and 40° C., and more typically between 20° C. and 35° C.

In some such above-described process embodiments, there further comprises use of a Fischer-Tropsch (sub)process in the converting of the hydrocarbonaceous assets.

In some such above-described process embodiments, the photobiofuels process involves harvesting of microalgae, wherein the process may further comprise a step of regulating microalgae metabolism at night, and wherein said regulation can comprise a method such as, but not limited to, (a) temperature modulation; (b) salinity modulation; (c) pH modulation; (d) modulation of $O_2$ concentration; and (e) combinations thereof.

In some such above-described process embodiments, the process further comprises the steps of: (a) storing at least a portion of the second super-atmospheric pressure $CO_2$-containing gas produced at night in containers of a type such as, but not limited to, above-ground gas tanks, underground salt domes, and combinations thereof; (b) recovering, during daylight hours, at least a portion the stored super-atmospheric pressure $CO_2$-containing gas; and (c) utilizing at least a portion of the $CO_2$ in the recovered second super-atmospheric pressure $CO_2$-containing gas to support photosynthesis in the photobiofuels process.

In some such above-described process embodiments, the process further comprises the production of $O_2$ in the photobiofuels process, wherein at least a portion of the $O_2$ is used to convert the hydrocarbonaceous assets, and wherein the $O_2$ can be used in a manner such as, but not limited to, (a) as a gaseous oxidant for synthesis gas production, (b) as an oxidant of synthesis gas to produce power, and (c) as combinations thereof; and wherein the photobiofuels process is a closed photobiofuels process.

In some such above-described process embodiments, the process further comprises the steps of, (a) storing at least a portion of $O_2$ produced in the photobiofuels process during daylight hours in containers selected from the group consisting of above-ground gas tanks, underground salt domes, and combinations thereof; (b) recovering, during the night, at least a portion the stored $O_2$; and (c) using at least a portion of the recovered $O_2$ in the converting of hydrocarbonaceous assets from, wherein the $O_2$ is used in a manner selected from the group consisting of (i) as a gaseous oxidant for synthesis gas production, (ii) as an oxidant of synthesis gas to produce power, and (iii) combinations thereof.

In some such above-described process embodiments, energy is created during the converting of hydrocarbonaceous assets, wherein said energy manifests itself in a form selected from the group consisting of electrical power, stream, hot gases, super-atmospheric pressure gases, and combinations thereof; and wherein at least a portion of this energy is utilized in the photobiofuels process in a manner selected from the group consisting of (a) stirring and pumping the liquid in the photobiofuels process, (b) sonicating the liquid, (c) processing the liquid in a high shear mixer, (d) separating microbes contained therein from the liquid, (e) drying microbes contained therein, (f) grinding, microbes contained therein to free lipids and other components, (g) separating the components, and (h) combinations thereof.

In some such above-described process embodiments, the process further comprises producing a methylester for use as a biodiesel, the producing, comprising the substeps of (a) recovering trigylcerides from the photobiofuels process; (b) transesterifying the trigylcerides from the photobiofuels process with an alcohol to form an ester and glycerin; and (c) purifying the ester; wherein at least a portion of the alcohol used in the transesterification is manufactured, in the process for converting hydrocarbonaceous assets, by synthesis gas conversion processes selected from the group consisting of methanol synthesis, Fisher-Tropsch, and combinations thereof. In some such embodiments, the alcohol is methanol. In some such embodiments, a liquid hydrocarbonaceous product is manufactured from the step of converting the hydrocarbonaceous assets; wherein this liquid is blended with at least a portion of the ester and/or triglyceride; and wherein the synthesis gas conversion process is a Fischer-Tropsch process.

In some such above-described process embodiments, the process further comprises the steps of: (a) removing a reduced nitrogen species from the $CO_2$-containing gas derived from the converting of hydrocarbonaceous assets, and (b) consuming the reduced nitrogen species in the photobiofuels process.

In some such above-described process embodiments, the step of converting the hydrocarbonaceous assets involves a Fischer-Tropsch process, wherein said process further comprises the steps of: (a) recovering triglycerides from the photobiofuels process; (b) recovering a product from the Fischer-Tropsch process, (c) processing at least a portion of both the triglyceride and the Fisher-Tropsch product in a hydroprocessing process to form paraffinic liquid hydrocarbonaceous products; and (d) recovering at least a portion of the paraffinic liquid hydrocarbonaceous products.

In some such above-described process embodiments, the process further comprises the steps of: (a) recovering triglycerides from the photobiofuels process; (b) converting the triglycerides to fatty acids, at least a portion of which are unsaturated; (c) oligomerizing the unsaturated fatty acids to form polyacids; and (d) esterifying the polyacids with an alcohol to form an unsaturated polyester operable for use as a synthetic lubricant. In some such embodiments, the process further comprises hydrogenating the unsaturated polyester to form a saturated polyester. In some such embodiments, at least a portion of the alcohol used in the esterification is manufactured in the step of converting the hydrocarbonaceous assets by a synthesis gas conversion processes selected from the group consisting of methanol synthesis, Fisher Tropsch, and combinations thereof. In some embodiments, the process further comprises a step of blending the polyester with a lubricant base oil made from a Fischer-Tropsch process. In some such embodiments, the Fisher-Tropsch process is used to convert the synthesis gas formed in the step of converting the hydrocarbonaceous assets.

4. AN INTEGRATED PROCESS COMPRISING AN ABSORPTION TOWER

As already mentioned, in alternate embodiments the present invention is directed to processes that integrate $CO_2$-producing conversions of hydrocarbonaceous assets with biofuels processes that utilize $CO_2$ in photosynthesis, wherein such processes involve the absorption of $CO_2$ in an absorption liquid, wherein such absorption is carried out in an absorption tower, and wherein at least some of the $CO_2$ captured by the absorption liquid is used to grow microbes or diatom species.

Figure 2:
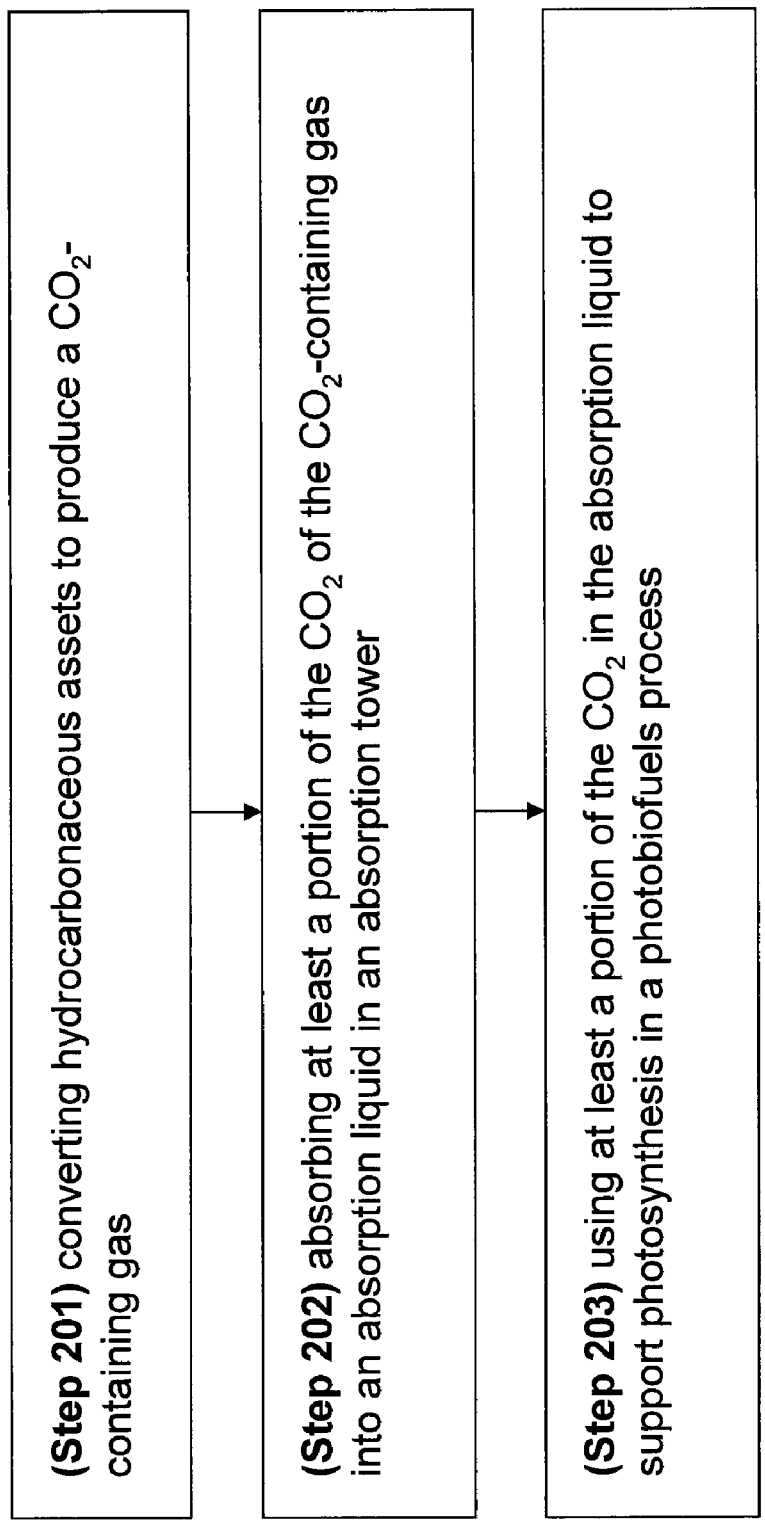
FIG. 2 depicts, in stepwise fashion, a process for integrating $CO_2$-producing conversions of hydrocarbonaceous assets with biofuels processes that utilize $CO_2$ for photosynthesis, wherein said process involves use of an absorption tower, in accordance with some alternate embodiments of the present invention.

Referring to the flow diagram of FIG. 2, in some embodiments, the present invention is directed to an integrated process for conversion of hydrocarbonaceous assets, the process comprising the steps of: (Step 201) converting hydrocarbonaceous assets to produce a $CO_2$-containing gas; (Step 202) absorbing at least a portion of the $CO_2$ of the $CO_2$-containing gas into an absorption liquid in an absorption tower, wherein the absorption liquid flows downward, and wherein the $CO_2$-containing gas flows upward; and (Step 203) using at least a portion of the $CO_2$ in the absorption liquid to support photosynthesis in a photobiofuels process.

Figure 3:
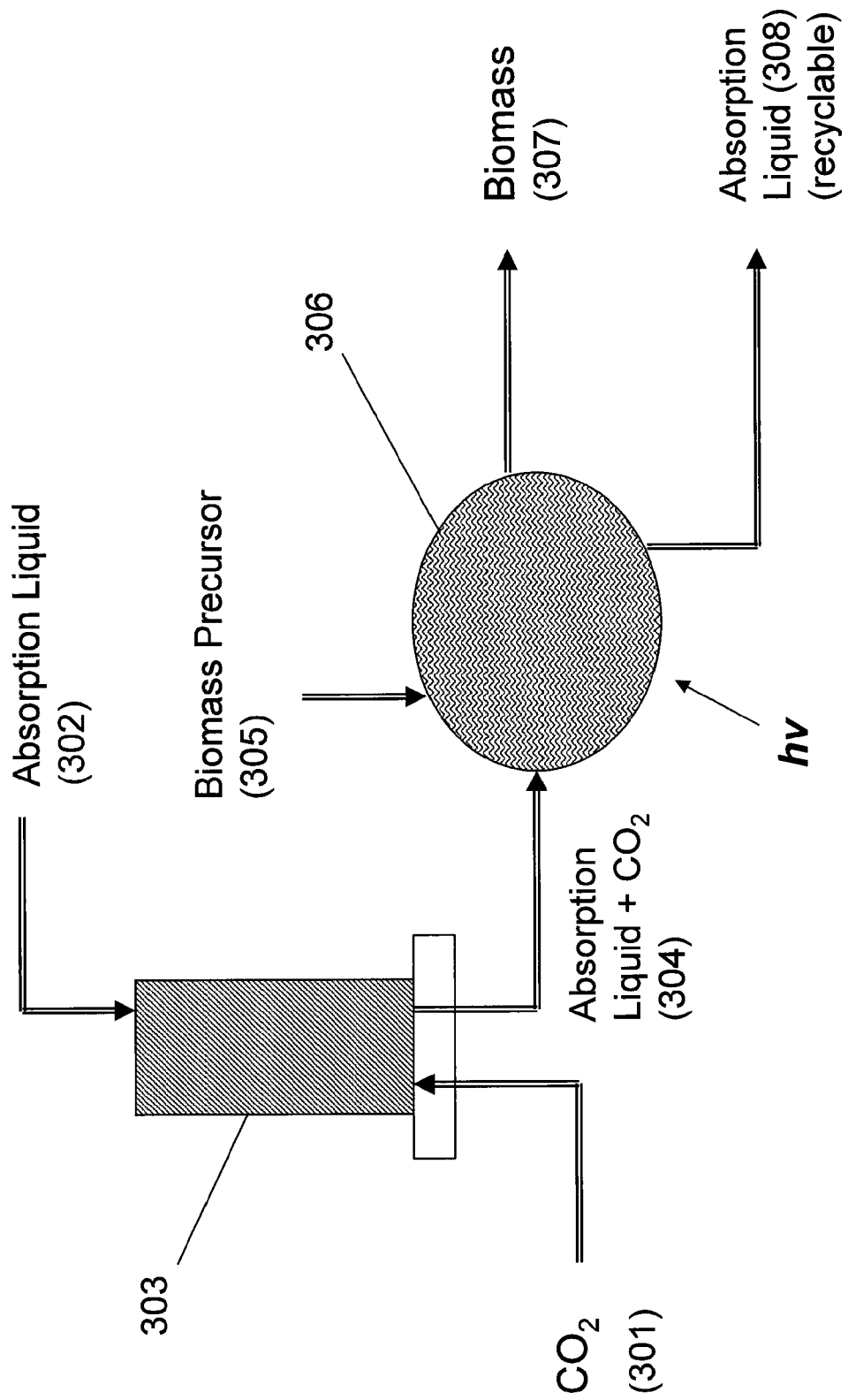
FIG. 3 illustrates, in flow diagram form, how an absorption tower can be utilized in the integrated process depicted in FIG. 2.

FIG. 3 illustrates how an absorption tower can be utilized in the above-described integrated processes. Referring to FIG. 3, $CO_2$ (301) from a hydrocarbonaceous asset conversion process is directed into an absorption tower 303 where it is absorbed by absorption liquid 302. The $CO_2$-laden absorption liquid 304 then leaves the tower and is combined with photosynthetically-responsive biomass precursor 305 in photosynthesis reactor 306 to grow/produce biomass 307. Note that the used absorption liquid can be recycled back into the absorption tower.

In some such above-described process embodiments, the process further comprises the steps of: (a) forming (e.g., growing) biomass in the absorption liquid used in the photobiofuels process; (b) removing the biomass to form a regenerated absorption liquid; and (c) recycling at least a portion of the regenerated absorption liquid to the absorption tower. In some such above-described process embodiments the absorption liquid is selected from the group consisting of water and caustic water. In some such above-described embodiments, the process further comprises forming water in the step of converting hydrocarbonaceous assets, and blending at least a portion of the water with the absorption liquid.

In some such above-described process embodiments, the process further comprises setting a target pH for the absorption liquid used in the photobiofuels process, and controlling the pH to this target by methods such as, but not limited to, (a) controlling blending of water from the converting of hydrocarbonaceous assets; (b) controlling temperature of the absorption liquid in the absorption tower, (c) controlling absorption liquid to gas ratio in the absorption tower; (d) controlling residence time of the absorption liquid in the absorption tower; and (e) combinations thereof. Typically, the target pH is greater than 6. More typically, the target pH is between 8 and 10.

In some such above-described process embodiments, the process further comprises setting a target salinity for the absorption liquid used in the photobiofuels reactor, and controlling the salinity to this target by controlled blending of water from the converting of hydrocarbonaceous assets. In some such embodiments, the salinity is measured in terms of conductivity, wherein the conductivity is typically less than 70 mmho·cm$^{-1}$, and more typically between 10 mmho·cm$^{-1}$ and 30 mmho·cm$^{-1}$.

In some such above-described process embodiments, a Fischer-Tropsch process is integrated with, and/or employed in, converting the hydrocarbonaceous assets. Such processes are described above.

In some such above-described process embodiments, the process further comprises setting a target temperature for the photobiofuels process, and controlling temperature to this target by use of gases and liquids from the converting of hydrocarbonaceous assets, said gases and liquids being selected from the group consisting of steam, condensate from steam, cold nitrogen gas, chilled water, and combinations thereof. The target temperature is typically between 10° C. and 40° C., and more typically between 20° C. and 35° C.

In some such above-described process embodiments, the photobiofuels process involves harvesting of microalgae, wherein the process further comprises a step of regulating microalgae metabolism at night, and wherein said regulation comprises a method such as, but not limited to, (a) temperature modulation; (b) salinity modulation; (c) pH modulation; modulation of $O_2$ concentration, and combinations thereof.

In some such above-described process embodiments, the process further comprises the steps of: (a) storing at least a portion of the absorption liquid from the absorption tower during nighttime operations in a tank; (b) recovering, during daylight hours, at least a portion the stored absorption liquid; and (c) utilizing at least a portion of the $CO_2$ in the recovered absorption liquid to support photosynthesis in the photobiofuels process.

In some such above-described process embodiments, the process further comprises the production of $O_2$ in the photobiofuels process and using at least a portion of the $O_2$ to convert the hydrocarbonaceous assets, wherein the $O_2$ is used in a manner such as, but not limited to, (a) as a gaseous oxidant for synthesis gas production, (b) as an oxidant of synthesis gas to produce power, and (c) as combinations thereof; and wherein the photobiofuels process is a closed photobiofuels process. In some such embodiments, the process further comprises the steps of: (a) storing at least a portion of $O_2$ produced in the photobiofuels process during daylight hours in containers selected from the group consisting of above ground gas tanks, underground salt domes, and combinations thereof; (b) recovering, during the night, at least a portion the stored $O_2$; and (c) using at least a portion of the recovered $O_2$ in the converting of hydrocarbonaceous assets from, wherein the $O_2$ is used in a manner selected from the group consisting of (i) as a gaseous oxidant for synthesis gas production, (ii) as an oxidant of synthesis gas to produce power, and (iii) combinations thereof.

In some such above-described process embodiments, energy is created during the converting of hydrocarbonaceous assets, wherein said energy manifests itself in a form such as, but not limited to, electrical power, stream, hot gases, superatmospheric pressure gases, and combinations thereof, and wherein at least a portion of this energy is utilized in the photobiofuels process in a manner such as, but not limited to, (a) stirring and pumping the liquid in the photobiofuels process, (b) sonicating the liquid, (c) processing the liquid in a high shear mixer, (d) separating microbes contained therein from the liquid, (e) drying microbes contained therein, (f) grinding microbes contained therein to free lipids and other components, (g) separating the components, and (h) combinations thereof.

In some such above-described process embodiments, the process further comprises producing a methylester for use as a biodiesel, the producing comprising the substeps of: (a) recovering trigylcerides from the photobiofuels process; (b) transesterifying the trigylcerides from the photobiofuels process with an alcohol to form an ester and glycerin; and (c) purifying the ester; wherein at least a portion of the alcohol used in the transesterification is manufactured, in the process for converting hydrocarbonaceous assets, by synthesis gas conversion processes selected from the group consisting of methanol synthesis, Fisher-Tropsch, and combinations thereof. In some such embodiments, the alcohol is methanol. In some or other such embodiments, a liquid hydrocarbonaceous product is manufactured from the step of converting the hydrocarbonaceous assets; wherein this liquid is blended with at least a portion of the ester and/or triglyceride; and wherein the synthesis gas conversion process is a Fischer-Tropsch process.

In some such above-described process embodiments, the process further comprises the steps of: (a) removing a reduced nitrogen species from the $CO_2$-containing gas derived from the converting of hydrocarbonaceous assets, and (b) consuming the reduced nitrogen species in the photobiofuels process.

In some such above-described process embodiments, the step of converting the hydrocarbonaceous assets involves a Fischer-Tropsch process, and wherein said process further comprises the steps of: (a) recovering triglycerides from the photobiofuels process; (b) recovering a product from the Fischer-Tropsch process; (c) processing at least a portion of both the triglyceride and the Fisher-Tropsch product in a hydroprocessing process to form paraffinic liquid hydrocarbonaceous products; and (d) recovering at least a portion of the paraffinic liquid hydrocarbonaceous products.

In some such above-described process embodiments, the process further comprises the steps of: (a) recovering triglycerides from the photobiofuels process; (b) converting the triglycerides to fatty acids, at least a portion of which are unsaturated; (c) oligomerizing the unsaturated fatty acids to form polyacids; and (d) esterifying the polyacids with an alcohol to form an unsaturated polyester operable for use as a synthetic lubricant. In some such embodiments, the process further comprises hydrogenating the unsaturated polyester to form a saturated polyester. In some or other such embodiments, at least a portion of the alcohol used in the esterification is manufactured in the step of converting the hydrocarbonaceous assets by a synthesis gas conversion processes selected from the group consisting of methanol synthesis, Fisher-Tropsch, and combinations thereof. In some or other such embodiments, the process can further comprise a step of blending the polyester with a lubricant base oil made from a Fischer-Tropsch process. In some or still other such embodiments, the Fisher-Tropsch process can be used to convert the synthesis gas formed in the step of converting the hydrocarbonaceous assets.

5. CONCLUSION

In summary, the present invention is generally directed to processes that integrate $CO_2$-producing conversions of hydrocarbonaceous assets with biofuels processes that utilize $CO_2$ in photosynthesis. In some embodiments, such processes involve the absorption of $CO_2$ in an absorption liquid. In some such embodiments, such absorption is carried out in an absorption tower. In some or other such embodiments, there is a subsequent desorption of the $CO_2$. Generally, at least some of the $CO_2$ captured by the absorption liquid is used to grow microbes or diatom species.

All patents and publications referenced herein are hereby incorporated by reference to the extent not inconsistent herewith. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed:

1. An integrated process comprising the steps of:
   a) converting at least one hydrocarbonaceous asset to produce a $CO_2$-containing gas;
   b) absorbing at least a portion of the $CO_2$ of the $CO_2$-containing gas into an absorption liquid in an absorption tower, wherein the absorption liquid flows downward, and wherein the $CO_2$-containing gas flows upward;
   c) collecting at least a portion of the $CO_2$-containing absorption liquid obtained in step (b) and, in a photobiofuels process, providing said collected $CO_2$-containing absorption liquid to support photosynthesis;
   d) forming an algal and/or diatomaceous biomass in the collected $CO_2$-containing absorption liquid;
   e) removing the formed biomass from the absorption liquid, thereby forming a regenerated absorption liquid;
   f) recycling at least a portion of the regenerated absorption liquid to the absorption tower;
   g) producing $O_2$ in the photobiofuels process; and
   h) providing at least a portion of said $O_2$ as (i) a gaseous oxidant for producing synthesis gas, (ii) an oxidant of synthesis gas for producing power therefrom, or (iii) combinations thereof;
   wherein the photobiofuels process is a closed photobiofuels process.

2. The process of claim 1, wherein the absorption liquid is selected from the group consisting of water and caustic water.

3. The process of claim 2, further comprising forming water in the step of converting hydrocarbonaceous assets, and blending at least a portion of the water with the absorption liquid.

4. The process of claim 3, further comprising setting a target pH for the absorption liquid used in the photobiofuels process, and controlling the pH to this target pH by methods selected from the group consisting of (a) controlling said blending of water from the converting of hydrocarbonaceous assets; (b) controlling temperature of the absorption liquid in the absorption tower; (c) controlling absorption liquid to gas ratio in the absorption tower; (d) controlling residence time of the absorption liquid in the absorption tower; and (e) combinations thereof.

5. The process of claim 4, wherein the target pH is greater than 6.

6. The process of claim 4, wherein the target pH is between 8 and 10.

7. The process of claim 3, further comprising setting a target salinity for the absorption liquid used in the photobiofuels process, and controlling the salinity to this target by controlled blending of water from the converting of said hydrocarbonaceous assets.

8. The process of claim 7, wherein the salinity is measured in terms of conductivity, and wherein the conductivity is less than 70 mmho·cm$^{-1}$.

9. The process of claim 8, wherein the conductivity is between 10 mmho·cm$^{-1}$ and 30 mmho·cm$^{-1}$.

10. The process of claim 3, wherein the converting of the hydrocarbonaceous assets comprises converting via a Fischer-Tropsch process.

11. The process of claim 1, further comprising setting a target temperature for the photobiofuels process, and controlling temperature to this target by providing gases and liquids from the converting of hydrocarbonaceous assets, said gases and liquids being selected from the group consisting of steam, condensate from steam, cold nitrogen gas, chilled water, and combinations thereof.

12. The process of claim 11, wherein the target temperature is between 10° C. and 40° C.

13. The process of claim 11, wherein the target temperature is between 20° C. and 35° C.

14. The process of claim 1, wherein the biomass is microalgae and wherein the photobiofuels process comprises (i) regulating the metabolism of said microalgae by modulating a temperature, salinity, and/or pH thereof and (ii) harvesting said microalgae.

15. The process of claim 1, further comprising the steps of:
    a) storing at least a portion of the absorption liquid from the absorption tower during nighttime operations in a tank;
    b) recovering, during daylight hours, at least a portion the stored absorption liquid; and
    c) providing at least a portion of the $CO_2$ in the recovered absorption liquid to support photosynthesis in the photobiofuels process.

16. The process of claim 1, wherein in step (g) the producing $O_2$ further comprising:
    (i) storing during daylight hours at least a portion of said produced $O_2$ in a container selected from the group consisting of an above ground gas tank, an underground salt dome, and combinations thereof; and
    (ii) recovering from the container during the night at least a portion of the stored $O_2$.

17. The process of claim 1, wherein energy is created during the converting of hydrocarbonaceous assets, wherein said energy manifests itself in a form selected from the group consisting of electrical power, stream, hot gases, super-atmospheric pressure gases, and combinations thereof; and wherein at least a portion of this energy is utilized in the photobiofuels process in a manner selected from the group consisting of (a) stirring and pumping the liquid in the photobiofuels process, (b) sonicating the liquid, (c) processing the liquid in a high shear mixer, (d) separating microbes contained therein from the liquid, (e) drying microbes contained therein, (f) grinding microbes contained therein to free lipids and other components, (g) separating the components, and (h) combinations thereof.

18. The process of claim 1, wherein in step (a) said converting the hydrocarbonaceous assets comprises forming a synthesis gas and converting the synthesis gas to methanol by a methanol synthesis reaction, a Fisher-Tropsch reaction, or a combination thereof; wherein the photobiofuels process is a triglyceride-producing process; and wherein the produced triglyceride is capable of being recovered from the photobiofuels process, transesterified with said methanol, and then purified to produce a methylester biodiesel.

19. The process of claim 18, wherein the synthesis gas converting process is a Fisher-Tropsch reaction.

20. The process of claim 1, wherein in step (a) said converting the hydrocarbonaceous assets further comprises removing from the $CO_2$-containing gas a reduced nitrogen species, and wherein the reduced nitrogen species is consumed in said photobiofuels process.

21. The process of claim 1, wherein the step of converting the hydrocarbonaceous assets involves a Fischer-Tropsch process, and wherein said process further comprises the steps of:
 a) recovering triglycerides from the photobiofuels process;
 b) recovering a product from the Fischer-Tropsch process;
 c) processing at least a portion of both the triglyceride and the Fisher-Tropsch product in a hydroprocessing process to form paraffinic liquid hydrocarbonaceous products; and
 d) recovering at least a portion of the paraffinic liquid hydrocarbonaceous products.

22. The process of claim 1, further comprising the steps of:
 a) recovering triglycerides from the photobiofuels process;
 b) converting the triglycerides to fatty acids, at least a portion of which are unsaturated;
 c) oligomerizing the unsaturated fatty acids to form polyacids; and
 d) esterifying the polyacids with an alcohol to form an unsaturated polyester operable for use as a synthetic lubricant.

23. The process of claim 22, further comprising hydrogenating the unsaturated polyester to form a saturated polyester.

24. The process of claim 22, wherein at least a portion of the alcohol used in the esterification is manufactured in the step of converting the hydrocarbonaceous assets by a synthesis gas conversion processes selected from the group consisting of methanol synthesis, Fisher-Tropsch, and combinations thereof.

25. The process of claim 22, further comprising a step of blending the polyester with a lubricant base oil made from a Fischer-Tropsch process.

26. The process of claim 21, wherein the Fisher-Tropsch process is used to convert the synthesis gas formed in the step of converting the hydrocarbonaceous assets.

* * * * *